(12) United States Patent
Corma Canós et al.

(10) Patent No.: US 8,765,993 B2
(45) Date of Patent: Jul. 1, 2014

(54) ONE-POT PRODUCTION OF CARBAMATES USING SOLID CATALYSTS

(75) Inventors: Avelino Corma Canós, Valencia (ES); Hermenegildo GarcíGómez, Valencia (ES); Raquel Juarez Marín, Valencia (ES)

(73) Assignees: Consejo Superior de Investigaciones Cientificas, Madrid (ES); Universidad Politecnica de Valencia, Valencia (ES)

( * ) Notice: Subject to any disclaimer, the term of this patent is extended or adjusted under 35 U.S.C. 154(b) by 149 days.

(21) Appl. No.: 13/228,815

(22) Filed: Sep. 9, 2011

(65) Prior Publication Data

US 2012/0053359 A1 Mar. 1, 2012

Related U.S. Application Data

(63) Continuation of application No. PCT/ES2010/070134, filed on Mar. 9, 2010.

(30) Foreign Application Priority Data

Mar. 10, 2009 (ES) .................................. 200900738

(51) Int. Cl.
C07C 271/06 (2006.01)

(52) U.S. Cl.
USPC ............................................................ 560/24

(58) Field of Classification Search
USPC .................................................... 560/24, 157
See application file for complete search history.

(56) References Cited

U.S. PATENT DOCUMENTS

2005/0222450 A1  10/2005  Gupte et al.

FOREIGN PATENT DOCUMENTS

| CN | 85109417 | 12/1986 |
| CN | 1304928 | 7/2001 |
| EP | 0 190 466 | 8/1986 |
| WO | 99/47493 | 9/1999 |
| WO | 2007/015852 | 2/2007 |
| WO | 2007/116111 | 10/2007 |
| WO | 2010/000888 | 1/2010 |

OTHER PUBLICATIONS

White et al. (Basic Energy Sciences Advisory Committee Subpanel Workshop Report, Opportunities for Catalysis in the 21st Century, 2002, pp. 1-47).*
Kang et al. ( Catalytic Performance of Supported PbO Catalysts for Synthesis of Methyl N-phenyl Carbamate from Aniline and Dimethyl Carbonate, Chinese Journal of Catalysis, vol. 28, No. 1, Jan. 2007).*
Kang et al. (Catalytic Performance of Supported PbO Catalysts for Synthesis of Methyl N-phenyl Carbamate from Aniline and Dimethyl Carbonate, Chinese Journal of Catalysis, vol. 28, No. 1, Jan. 2007, Translated on May 26, 2013 by the McElroy Translation Company).*
International Search Report issued Jun. 23, 2010 in International (PCT) Application No. PCT/ES2010/070134.
R. Juárez et al., "Gold-Catalyzed Phosgene-Free Synthesis of Polyurethane Precursors", Angew. Chem. Int. Ed., 2010, vol. 49 n° 7, pp. 1286-1290.
A.M. Tafesh et al., "A Review of the Selective Catalytic Reduction of Aromatic Nitro Compounds into Aromatic Amines, Isocyanates, Carbamates, and Ureas Using CO", Chem. Rev., 1996, vol. 96, pp. 2035-2052.

* cited by examiner

*Primary Examiner* — Brandon Fetterolf
*Assistant Examiner* — Blaine G Doletski
(74) *Attorney, Agent, or Firm* — Wenderoth, Lind & Ponack, L.L.P.

(57) ABSTRACT

The invention relates to the production of carbamates in a single reactor (one-pot) using solid catalysts, involving the reaction between at least one nitro compound, an organic carbonate of formula (OR)(OR')C=O, a gas selected from hydrogen gas and a mixture of gases containing hydrogen and hydrogen precursor compounds, and a catalyst that has at least one metallic oxide and can also contain an element of groups 8, 9, 10 and 11 of the periodical table. The carbonates obtained can be transformed into their corresponding isocyanates.

22 Claims, No Drawings

ONE-POT PRODUCTION OF CARBAMATES USING SOLID CATALYSTS

This application is a Continuation of International Application No. PCT/ES2010/070134, filed Mar. 9, 2010.

FIELD OF THE INVENTION

The present invention relates to a method for the production of carbamates by reaction of nitro compounds with organic carbonates in the presence of hydrogen and heterogeneous catalysts.

STATE OF THE ART

Organic carbamates are compounds widely used in many applications including pharmaceutical preparations and production of agro-compounds (pesticides and herbicides). Of particular relevance is the use of carbamates as precursors in the synthesis of isocyanates that can be used as monomers in the synthesis of polyurethanes.

One of the industrial processes for the synthesis of polyurethanes is based on obtaining isocyanates by reacting amines with phosgene. The toxicity of phosgene determines that it is highly desirable to find alternatives to this reagent for the preparation of isocyanates. In this regard, one possible alternative route for synthesizing isocyanates from amines consists of using carbamates as intermediates. The preparation of carbamates may be carried out by reaction of organic carbonates with amines (P200802101) without the need of using phosgene.

However, dialkyl carbonates can react with amines in two different ways. By forming carbamates or by forming N-alkylation products. This second reaction acts competing with the first and it is undesirable when the aim is the selective synthesis of carbamates (Scheme 1).

Scheme 1

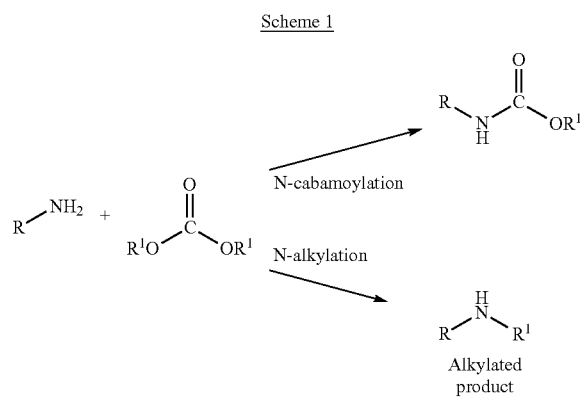

The most widely used organic carbonate and that has received more attention because of its accessibility is dimethyl carbonate, although other dialkyl carbonates and alicyclic carbonates may act similarly to dimethyl carbonate and can act in the presence of amines as alkylating or carbamoylating agents. Other organic carbonates that may be employed are aromatic carbonates such as diphenyl carbonate or carbonates with polyfluorinated alkyl groups.

Another possibility for obtaining carbamates would be obtaining them directly from nitro compounds through reduction of the nitro compound and subsequent carbamoylation.

The carbamate formation reaction from nitro compounds has been extensively studied and reported in the literature. Most of the experiments described relate to obtaining organic carbamates by means of reductive carbonylation of nitroaromatic compounds using palladium and CO complexes as carbonylation agent (IT1318396, Michela Gasperini et al. Adv. Synthesis Catalist 2005, 347, 105-120; Petra Wehman et al. Organometallics 1994, 13, 4856-4869). There are other references describing the reaction of nitroaromatics to give carbamates: Ragaini, F., Cenini, S. & Querci, C. in Belg. FIELD Full Journal Title: 22 pp. ((Eni S.p.A., Italy; Enichem S.p.A.). Be, 2002); Dahlhaus, J. & Hoehn, A. in Ger. Offen. FIELD Full Journal Title: 7 pp. ((BASF A.-G., Germany). De, 1997); Yamada, M., Murakami, K., Nishimura, Y., Nakajima, F. & Matsuo, N. in Eur. Pat. Appl. FIELD Full Journal Title: 10 pp. ((Babcock-Hitachi K. K., Japan). Ep, 1990); Drent, E. & Van Leeuwen, P. W. N. M. in Eur. Pat. Appl. FIELD Full Journal Title: 23 pp. ((Shell Internationale Research Maatschappij B. V., Neth.). Ep, 1983); Stapersma, J. & Steernberg, K. in Eur. Pat. Appl. FIELD Full Journal Title: 7 pp. ((Shell Internationale Research Maatschappij B. V., Neth.). Ep, 1988).

Thus it has been described that nitroaromatic compounds react with 3 equivalents of carbon monoxide in an alcoholic medium to form carbamates.

Scheme 1. Reduction of nitrobenzene with carbon monoxide in the presence of methanol to form N-phenylcarbamate.

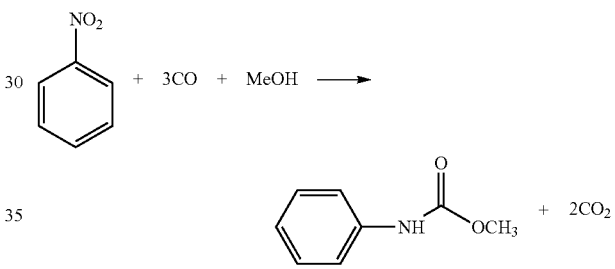

The methods proposed in the mentioned technique for producing carbamates by reaction of nitro compounds and CO have a number of disadvantages. First, the use of soluble metal catalysts (typically Pd) for the mentioned reaction requires costly processes to recover the catalyst and to obtain carbamates with the purity required for its further industrial use. In addition, these catalysts generally lose their activity in the course of the reaction, and in the case of being recovered, they cannot be recycled to the process, which implies a relatively high cost of catalyst and the formation of undesirable metal waste from the environmental point of view. In addition, some processes produce an excessive amount of N-alkylation and/or low carbamoylation yield, further requiring elevated temperatures and/or relatively long reaction times.

Another drawback is that the process generates two equivalents of carbon dioxide per equivalent of carbamate formed. In this context, those series of processes that do not generate $CO_2$ (neutral $CO_2$) are the most interesting from an environmental point of view. Therefore, when the starting products directly or indirectly (the case of organic carbonates) consume carbon dioxide are more attractive than those that start from carbon monoxide, which is obtained by gasification of coal or hydrocarbons.

DESCRIPTION OF THE INVENTION

The present invention relates to a method for preparing carbamates in a "one pot" single reactor characterized in that it comprises the reaction between at least:

a nitro compound,
an organic carbonate of the formula (OR)(OR')C=O,
a gas selected from hydrogen gas, a mixture of gases containing hydrogen and hydrogen precursor compounds,
a catalyst comprising at least one metallic oxide, preferably selected from $CeO_2$, $ZrO_2$, $La_2O_3$, $TiO_2$, $Y_2O_3$ and combinations thereof, more preferably $CeO_2$.

Said method may have the following reaction scheme:

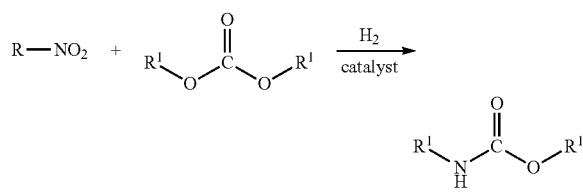

Processes in a single reactor (one pot) are a strategy intended to enhance processes for improving the efficiency of reactions where a reactant is subjected to successive chemical reactions in a single reactor. These reactions are being extensively studied due to their numerous advantages such as the elimination of the processes of separation and purification of intermediates with a consequent increase of production and decrease of investment and formation of waste.

According to a preferred embodiment of the method of the invention, the catalyst further comprises one of the metallic oxides described above, at least one element from groups 8, 9, 10, 11 and combinations thereof, preferably Fe, Au, Pt, Pd, Cu, Ag, Co, Rh, Ir and combinations thereof. Said element is preferably Au.

Metallic oxides can be used as support. The particle size of the support can be comprised between several nanometers and several microns. Oxide may be stoichiometric or the ratio between metal and oxygen may differ from that expected based on the valences of the elements. As already mentioned, these metallic oxides exhibit intrinsic catalytic activity promoting the reaction of N-carbamoylation between amines formed in situ in the hydrogenation of nitro compounds and organic carbonates. It has also been found that the catalytic efficiency inherent to metallic oxides in terms of reaction rate can be improved in some cases with the deposition of nanoparticles of an element according to the reaction conditions.

The preferred particle size of the metallic oxide comprising the aforementioned catalyst is between 1 and 50 nm.

According to a preferred embodiment, the element or elements that can be added to the metallic oxide or any combination thereof may be in a percentage preferably between 0.01 and 10% by weight with respect to the catalyst, more preferably between 0.1 and 6%. In addition, said element may have a particle size selected from between 1 and 20 nm, more preferably between 2 and 10 nm.

According to a preferred embodiment, the catalyst further comprises an alkali or alkaline-earth metal. This metal can be preferably Na.

According to a particular embodiment, the method is carried out at a temperature preferably between 20 and 250° C., more preferably between 90 and 160° C. and at a pressure preferably between 1 and 20 bars, more preferably between 2 and 10 bars.

In the present invention it has been found that nanoparticulate metallic oxides containing one or more elements are able to selectively catalyze the reaction between a nitro compound and an organic carbonate in the presence of a reducing gas such as for example $H_2$.

In cases where the catalyst comprises at least one second element, the size of the nanoparticles of said element is important for the catalytic activity because the activity of the catalyst is greatly reduced when the particles containing the element or elements of groups 8, 9, 10 and 11 exceed a size of 20 nm. A more suitable particle size according to the method of the present invention would be between 1 and 20 nm, preferably between 2 and 10 nm.

It has been observed in the present study that, for example, cerium oxide with nanometric particle size (>20 nm) exhibits a catalytic activity to promote carbamoylation of amines that can be generated in situ by reduction of nitro compounds.

To carry out the carbamoylation reaction of nitro compounds in one single process by coupling two reactions, for example, temperatures between 20 and 200° C., and pressure sufficient to maintain the reactants in liquid phase can be used.

Thus a preferred embodiment of the present invention consists of 0.1-2% by weight of Au with crystal size between 2 and 5 nm on cerium oxide.

The carbonates used according to the method of the present invention can be, at least one organic carbonate of formula (OR)(OR')C=O, where R and R' can be selected from substituted alkyl groups from 1 to 20 carbon atoms, substituted aryl groups and non-substituted aryl groups.

According to a preferred embodiment R and R' are identical and are simple alkyl groups such as methyl or ethyl. Preferably, the carbonate may be selected from dimethyl carbonate and diethyl carbonate.

Among the cyclic carbonates the derivatives of ethylene glycol, propylene glycol and glycerin are especially important.

According to a preferred embodiment, R and R' may be fluorinated alkyl groups. According to this preferred embodiment, the organic carbonate may be selected from bis(2-fluoroethyl) carbonate, bis(3-fluoropropyl) carbonate, bis(2,2,2-trifluoroethyl) carbonate, bis(1,3-difluoro-2-propyl) carbonate, bis(1,1,1-trifluoro-2-propyl) carbonate, bis(2,2,3,3-tetrafluoro propyl) carbonate, bis(2,2,3,3,3-pentafluoropropyl) carbonate, bis(1-fluoro-2-butyl) carbonate, bis(2-fluoro-1-butyl) carbonate, bis(1-fluoro-2-methyl-2-propyl) carbonate, bis(2-fluoro-2-methyl-1-propyl) carbonate, bis(1H,1H,2H,2H-perfluoro-1-hexyl) carbonate, bis(perfluorooctyl) carbonate, bis(1,1,1,3,3,3-hexafluoro-2-propyl) carbonate, preferably bis(2,2,2-trifluoroethyl) carbonate.

In addition, the method of the present invention comprises among others, a nitro compound of formula $R(NO_2)_n$ where R is selected from the group consisting of substituted or non-substituted alkyl with 1 to 20 carbon atoms, substituted or non-substituted aryl with 6 to 15 carbon atoms, substituted or non-substituted arylalkyl with 7 to 15 carbon atoms, substituted or non-substituted alkenyl with 2 to 20 carbon atoms, substituted or non-substituted alkynyl with 2 to 20 carbon atoms, substituted or non-substituted cycloalkyl with 3 to 20 carbon atoms, substituted or non-substituted cycloalkenyl with 4 to 20 carbon atoms and substituted or non-substituted cycloalkynyl with 5 to 20 carbon atoms; and n is 1, 2, 3, 4, 5 or 6.

According to a preferred embodiment, the compound is an aromatic nitro compound that is selected from the group consisting of nitrobenzene, nitrotoluene, 2,4-dinitrotoluene, 1,3-dinitrobenzene, bis(nitrophenyl)methane.

According to another preferred embodiment, the nitro compound can be selected from nitrogen heterocycles of five and six members with nitro groups.

According to another preferred embodiment, the nitro compound is an aliphatic compound wherein the aliphatic chain contains from 1 to 20 carbons. More preferably the aliphatic nitro compound is selected from nitromethane, nitroethane, nitroethene, 1,4-dinitrobutane, 1,6-dinitrohexane, 1,8-dinitrooctane, 1,10-dinitrododecane and 1,12-dinitrodecane.

The method of the present invention enables obtaining aliphatic and aromatic carbamates from nitro compounds in high yield and high purity while the heterogeneous nature of the solid catalyst facilitates its separation, recovery and reuse. The carbamates obtained according to the method of the present invention can also be transformed into the corresponding isocyanate, for example by heat treatment or by reaction in basic medium or with the use of catalysts.

Throughout the description and claims the word "comprises" and its variants are not intended to exclude other technical features, additives, components, or steps. For those skilled in the art, other objects, advantages and features of the invention will become apparent in part from the description and in part from the practice of the invention. The following examples are provided by way of illustration and are not intended to be limiting of the present invention.

EXAMPLES

Next non-limiting examples of the present invention will be described.

Example 1

Formation of 2,4-bis(methoxycarbonylamino) toluene

In a 5 ml reinforced glass flask capable of pressure sealing dimethyl carbonate (2 ml), 2,4-dinitrotoluene (150 mg), the Au/CeO$_2$ catalyst (100 mg, 1 wt % gold relative to cerium) are placed, and the reactor is closed. After purging with N$_2$ for 5 minutes, the reactor is loaded with hydrogen gas at a pressure of 15 bars. The reactor is immersed in a silicone bath preheated at 150° C. and the mixture is magnetically stirred for 23 hrs. After this time, the reactor is brought to atmospheric pressure and opened. The catalyst is filtered and the liquid phase is analyzed by gas chromatography. The disappearance of 2,4-dinitrotoluene and the formation of 2,4-bis(methoxycarbonylamino) toluene in a 63% yield is observed. Smaller amounts (20%) of ortho and para mixtures of the mono carbamoylate 2,4-diaminotoluene derivative are detected.

Example 2

Formation of the O-methyl N-phenyl carbamate

In a 5 ml reinforced glass flask capable of pressure sealing dimethyl carbonate (2 ml), nitrobenzene (125 mg), the Au/CeO$_2$ catalyst (100 mg, 1 wt % gold relative to cerium) are placed and the reactor is closed. After purging with N$_2$ for 5 minutes, the reactor is loaded with hydrogen gas at a pressure of 15 bars. The reactor is immersed in a silicone bath preheated at 150° C. and the mixture is magnetically stirred for 23 hrs. After this time, the reactor is brought to atmospheric pressure and opened. The catalyst is filtered and the liquid phase is analyzed by gas chromatography. The formation of O-methyl N-phenyl carbamate in a 50% yield is observed. The presence of aniline (20%) is observed, while the presence of starting nitrobenzene is not detected.

Example 3

Formation of 1,6-bis(methoxycarbonylamino) hexane

In a reinforced glass reactor with a capacity of 5 ml 2 ml of dimethyl carbonate and 150 mg of 1,6-dinitrohexane and 100 mg of Au/CeO$_2$ (1 wt % gold relative to cerium) are introduced. The reactor is closed and purged with N$_2$ to remove oxygen from the solution. Then the reactor is charged at 15 bars of hydrogen and immersed in a silicone bath preheated at 90° C. The suspension is magnetically stirred for 8 hrs. After this time, the reactor is discharged at atmospheric pressure, opened and the mixture is filtered. A gas chromatography analysis revealed the presence of 1,6-bis (methoxycarbonylamino) hexane in an 85% yield.

Example 4

Formation of 1,3-bis(methoxycarbonylamino) toluene

In a 5 ml reinforced glass flask capable of pressure sealing dimethyl carbonate (2 ml), meta-dinitrobenzene (150 mg), the Au/CeO$_2$ catalyst (100 mg, 1 wt % gold relative to titanium) are placed. A magnetic stirrer is added and it is proceeded to close the reactor. After purging with N$_2$ for 5 minutes, the reactor is loaded with hydrogen gas at a pressure of 15 bars. The reactor is immersed in a silicone bath preheated at 150° C. and the mixture is magnetically stirred for 23 hrs. After this time, the reactor is brought to atmospheric pressure and opened. The catalyst is filtered and the liquid phase is analyzed by gas chromatography. The formation of 1,3-bis (methoxycarbonylamino) benzene in a 60% yield is observed. Smaller amounts (20%) of mono carbamoylate 1,3-diaminobenzene are detected.

Example 5

Formation of 2,4-bis(ethoxycarbonylamino) toluene

It is carried out similar to the protocol described in Example 1 but using the same amount of diethyl carbonate instead of dimethyl carbonate. After carrying out the reaction at 160° C. for 24 hrs, the analysis of the reaction crude reveals the presence of 2,4-bis(ethoxycarbonylamino) toluene in a 50% yield. Smaller amounts (15%) of ortho and para mixtures of the mono carbamoylate 2,4-diaminotoluene derivative were detected.

Example 6

Reuse of the Au/CeO$_2$ catalyst

It is carried out as described in Example 1. After the reaction, and after separating the liquid phase, the solid catalyst is collected from the nylon filter, washed with methanol, let it dry and used in a reaction using the same quantities of reagent and procedural conditions set out in Example 1. After 12 hrs, the reaction mixture is filtered and analyzed by gas chromatography yielding the same results, i.e. 63% 2,4-bis(methoxycarbonylamino) toluene, indicated in Example 1.

The reuse of the catalyst was carried out a third time, and operating under the same conditions, a 60% yield of 2,4-bis (methoxycarbonylamino) toluene was obtained.

Example 7

Formation of 2,4-bis(methoxycarbonylamino) toluene Catalyzed by Cerium Oxide Nanoparticles The catalyst of the present example is a nanoparticulate cerium oxide which is prepared by hydrolysis of a cerium nitrate solution at pH 8 using an aqueous ammonium hydroxide (20 wt %) solution as a base to adjust the pH. The resulting $CeO_2$ colloidal solution is subjected to dialysis until removing the nitrates and subsequently the nanocrystalline $CeO_2$ is recovered by centrifugation. The n-hydrogenation/carbamoylation reaction of 2,4-dinitrotoluene is carried out as described in Example 1 but using $CeO_2$ (231.8 mg) as a catalyst whereby after 23 hrs of reaction was obtained a mixture wherein the conversion of 2,4-dinitrotoluene was 53%, being present the 2,4-diaminotoluene compound with a selectivity of 10% and a mixture of the corresponding dicarbamate in a 90% overall selectivity.

Example 8

Formation of 2,4-bis(methoxycarbonylamino) toluene Catalyzed by Gold Nanoparticles Supported on Nanoparticle Cerium Oxide Doped with Na+

The catalyst of the present example is an $Au/CeO_2$ (263.6 mg) which is subjected to further treatment consisting of impregnation with sodium bicarbonate (3.2 mg) in order to neutralize by doping the possible acid centers of the surface of the nanocrystalline cerium oxide. The carbamoylation reaction of the 2,4-diaminotoluene is carried out as described in Example 1 but using as a catalyst $Au/(Na^+)CEO_2$ (208.2 mg) whereby after 23 hrs of reaction was obtained a mixture wherein the conversion of 2,4-dinitrotoluene was 96%, being present the 2,4-diaminotoluene and the corresponding dicarbamate with a selectivity of 37 and 63%, respectively.

Example 9

Formation of 2,4-bis(methoxycarbonylamino) toluene Catalyzed by Gold Nanoparticles (Interior)-Palladium (exterior) Supported on Titanium Oxide in Anatase Phase The catalyst is prepared as described in the state of the art (Enache, D. I. et al. Solvent-Free Oxidation of Primary Alcohols to Aldehydes Using Au—Pd/$TiO_2$ Catalysts. Science 311, 362-365 (2006)). This catalyst consists of gold nanoparticles decorated with palladium nanoparticles that are supported on the commercial titanium oxide designated P-25 (Degusa). The load of gold is 0.8% and palladium is 0.5%, both by weight.

With this catalyst and operating as described in Example 1 after 24 hrs of reaction a mixture is obtained wherein the conversion of 2,4-dinitrotoluene was 95% and containing 5% 2,4-diaminotoluene together with a mixture of mono- and dicarbamate derivatives of the aromatic diamine at 87%.

The invention claimed is:

1. A one pot method for preparing carbamates in a single reactor, comprising a reaction between at least:
   a nitro compound,
   an organic carbonate of the formula (OR)(OR')C=O wherein R and R' are each independently selected from substituted alkyl groups having between 1 to 20 carbon atoms, substituted aryl groups and non-substituted aryl groups, or R and R' are identical and selected from methyl and ethyl,
   a gas selected from hydrogen gas, and a mixture of gases containing hydrogen and hydrogen precursor compounds, and
   a catalyst selected from $CeO_2$, $TiO_2$, $Au/CeO_2$, interior gold nanoparticles-exterior palladium nanoparticles supported on $TiO_2$ in anatase phase, a metal from group 10 or 11 supported on $CeO_2$ or $TiO_2$, and an alkali metal supported on $Au/CeO_2$.

2. The method according to claim 1, wherein the metallic oxide comprising the catalyst has a particle size of between 1 and 50 nm.

3. The method according to claim 1, wherein the gold or the combination of gold and palladium comprised in the catalyst is in a percentage between 0.01 and 10 wt %.

4. The method according to claim 3, wherein the gold or the combination of gold and palladium comprised in the catalyst is in a percentage between 0.1 and 6 wt %.

5. The method according to claim 1, wherein the particles containing gold or the combination of gold and palladium have a particle size between 1 and 20 nm.

6. The method according to claim 5, wherein the particles containing gold or the combination of gold and palladium have a particle size between 2 and 10 nm.

7. The method according to claim 1, wherein the reaction is carried out at a temperature between 20 and 250° C.

8. The method according to claim 1, wherein the reaction is carried out at a pressure between 1 and 20 bars.

9. The method according to claim 1, wherein the catalyst is $Au/CeO_2$ and is further doped with $Na^+$.

10. The method according to claim 1, wherein the carbonate is dimethyl carbonate.

11. The method according to claim 1, wherein the carbonate is diethyl carbonate.

12. The method according to claim 1, wherein the carbonate is selected from carbonates derived from ethylene glycol, propylene glycol or glycerin.

13. The according to claim 1, wherein R and R' are fluorinated alkyl groups.

14. The method according to claim 13, wherein the carbonate is selected from bis(2-fluoroethyl) carbonate, bis(3-fluoropropyl) carbonate, bis(2,2,2-trifluoroethyl) carbonate, bis(1,3-difluoro-2-propyl) carbonate, bis(1,1,1-trifluoro-2-propyl) carbonate, bis(2,2,3,3-tetrafluoro propyl) carbonate, bis(2,2,3,3,3-pentafluoropropyl) carbonate, bis(1-fluoro-2-butyl) carbonate, bis(2-fluoro-1-butyl) carbonate, bis(1-fluoro-2-methyl-2-propyl) carbonate, bis(2-fluoro-2-methyl-1-propyl) carbonate, bis(1H,1H,2H,2H-perfluoro- 1-hexyl) carbonate, bis(perfluorooctyl) carbonate, bis(1,1,1,3,3,3-hexafluoro-2-propyl) carbonate.

15. The method according to claim 14, wherein the carbonate is bis(2,2,2-trifluoroethyl) carbonate.

16. The method according to claim 1, wherein the nitro compound is represented by the formula

$$R(NO_2)_n$$

where R is selected from the group consisting of substituted or non-substituted alkyl with 1 to 20 carbon atoms, substituted or non-substituted aryl with 6 to 15 carbon atoms, substituted or non-substituted arylalkyl with 7 to 15 carbon atoms, substituted or non-substituted alkenyl with 2 to 20 carbon atoms, substituted or non-substituted alkynyl with 2 to 20 carbon atoms, substituted or non-substituted cycloalkyl with 3 to 20 carbon atoms, substituted or non-substituted cycloalkenyl with 4 to 20 carbon atoms and substituted or non-substituted cycloalkynyl with 5 to 20 carbon atoms; and n is 1, 2, 3, 4, 5 or 6.

17. The method according to claim 16, wherein the nitro compound is an aromatic nitro compound.

18. The method according to claim 17, wherein the nitro compound is selected from nitrobenzene, nitrotoluene, 2,4-dinitrotoluene, 1,3-dinitrobenzene, bis(nitrophenyl) methane.

19. The method according to claim 16, wherein the nitro compound is an aliphatic compound wherein the aliphatic chain contains between 1 and 20 carbons.

20. The method according to claim 19, wherein the aliphatic nitro compound is selected from nitromethane, nitroethane, nitroethene, 1,4-dinitrobutane, 1,6-dinitrohexane, 1,8-dinitrooctane, 1,10-dinitrododecane and 1,12-dinitrodecane.

21. The method according to claim 1, wherein the method further comprises transforming the carbamates obtained in a corresponding isocyanate.

22. The method according to claim 1, wherein the catalyst is $CeO_2$ nanoparticles.

* * * * *

UNITED STATES PATENT AND TRADEMARK OFFICE
CERTIFICATE OF CORRECTION

PATENT NO. : 8,765,993 B2  
APPLICATION NO. : 13/228815  
DATED : July 1, 2014  
INVENTOR(S) : Avelino Corma Canos et al.

It is certified that error appears in the above-identified patent and that said Letters Patent is hereby corrected as shown below:

In the Specification and in the Claims

In column 5, lines 6-7, and column 9, line 16-17, claim 20, please replace "1,10-dinitrododecane" and "1,12-dinitrodecane" with -- 1,10-dinitrodecane -- and -- 1,12-dinitrododecane --, respectively.

Signed and Sealed this
Second Day of December, 2014

Michelle K. Lee
*Deputy Director of the United States Patent and Trademark Office*